United States Patent [19]

Teraji et al.

[11] Patent Number: 4,563,449
[45] Date of Patent: Jan. 7, 1986

[54] CEPHEM COMPOUNDS

[75] Inventors: Tsutomu Teraji, Osaka; Kazuo Sakane, Amagasaki; Jiro Goto, Suita, all of Japan

[73] Assignee: Fujisawa Pharmaceutical Co., Ltd., Osaka, Japan

[21] Appl. No.: 511,237

[22] Filed: Jul. 6, 1983

[30] Foreign Application Priority Data

Jul. 19, 1982 [GB]  United Kingdom ............... 8220833
Mar. 2, 1983 [GB]  United Kingdom ............... 8305799

[51] Int. Cl.$^4$ ............... C07D 501/38; A61K 31/545
[52] U.S. Cl. ........................... 514/203; 544/25; 544/26; 544/27; 514/206; 514/204
[58] Field of Search ............... 544/25, 22, 21, 26, 544/27, 28, 30; 424/246; 514/203, 204, 206

[56] References Cited

U.S. PATENT DOCUMENTS 4,331,665  5/1982  Terajii et al. ............... 544/25
4,443,444  4/1984  Takaya et al. ............... 544/25

OTHER PUBLICATIONS

McOomie, Protective Groups in Organic Chemistry (1973), pp. 71–72, Plenum Press.
Greene, Protective Groups in Organic Chemistry (1981), John Wiley and Sons.

Primary Examiner—Nicholas S. Rizzo
Attorney, Agent, or Firm—Oblon, Fisher, Spivak, McClelland & Maier

[57] ABSTRACT

The invention relates to novel cephem compounds of high antimicrobial activity of the formula:

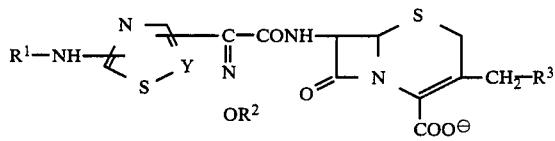

wherein $R^1$ is phosphono, dihalophosphoryl, di(lower) alkoxyphosphoryl, O-lower alkylphosphono, diaminophosphoryl, (anino) (hydroxy) phosphoryl or (lower alkoxy) (morpholino) phosphoryl, $R^2$ is lower alkyl or lower alkenyl, $R^3$ is a group of the formula:

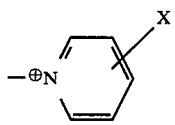

wherein X is hydrogen, halogen or lower alkoxy, or a group of the formula:

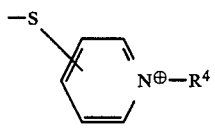

wherein $R^4$ is lower alkyl, and Y is N or CH; and pharmaceutically acceptable salts thereof.

8 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

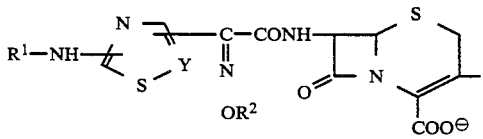

(I)

wherein
$R^1$ is phosphono or protected phosphono;
$R^2$ is lower aliphatic hydrocarbon group;
$R^3$ is pyridinio or pyridiniothio; each of which may have suitable substituent(s), and
Y is N or CH.

According to the present invention, the new cephem compounds (I) can be prepared by processes which are illustrated in the following scheme.

Process 1

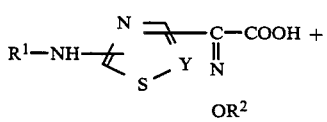

(II)
or its reactive
derivative at the
carboxy group
or a salt thereof

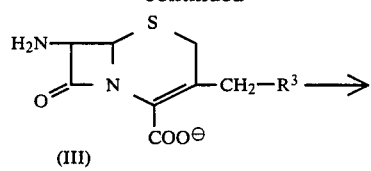

(III)
or its reactive
derivative at the
amino group
or a salt thereof

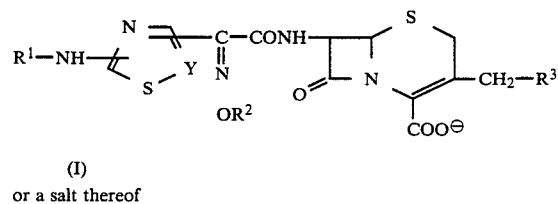

(I)
or a salt thereof

Process 2

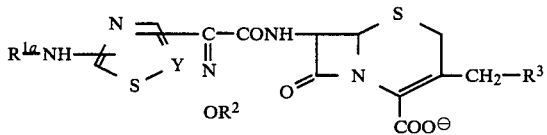

(Ia)
or a salt thereof

Elimination of
protective group
of phosphono

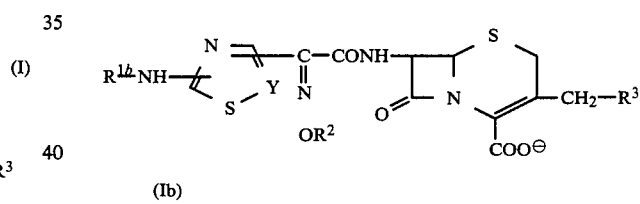

(Ib)
or a salt thereof

Process 3

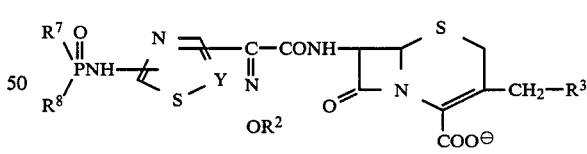

(Id)
or a salt thereof

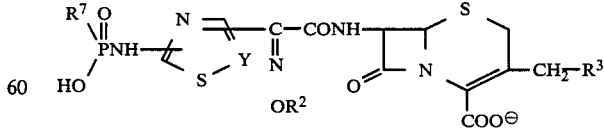

(Ie)
or a salt thereof wherein $R^1$, $R^2$, $R^3$ and Y are each as defined above, $R^{1a}$ is a protected phosphono, $R^{1b}$ is phosphono, $R^7$ is amino or lower alkoxy and $R^8$ is amino or morpholino.

Among the starting compounds of the present invention, the compound (II) is novel and can be prepared by the following methods.

Preparation 1

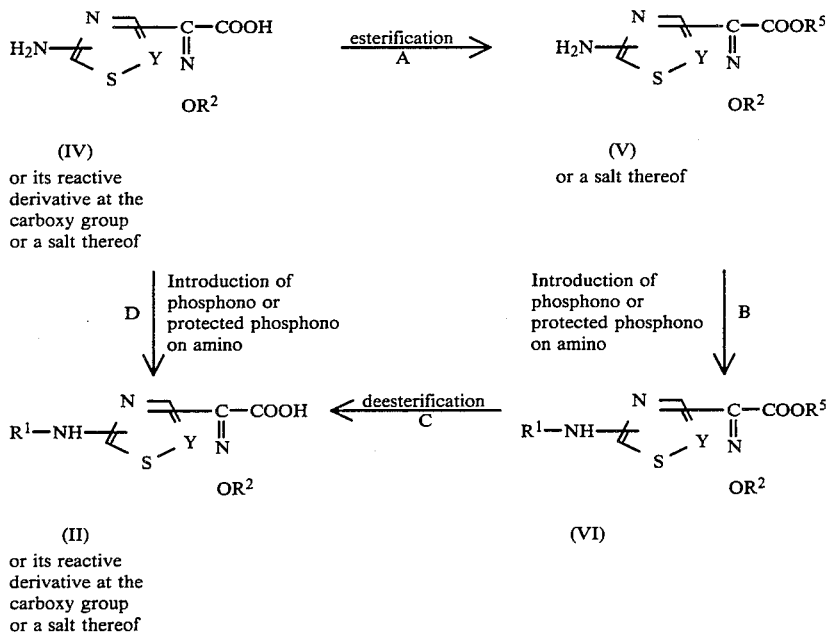

Preparation 2

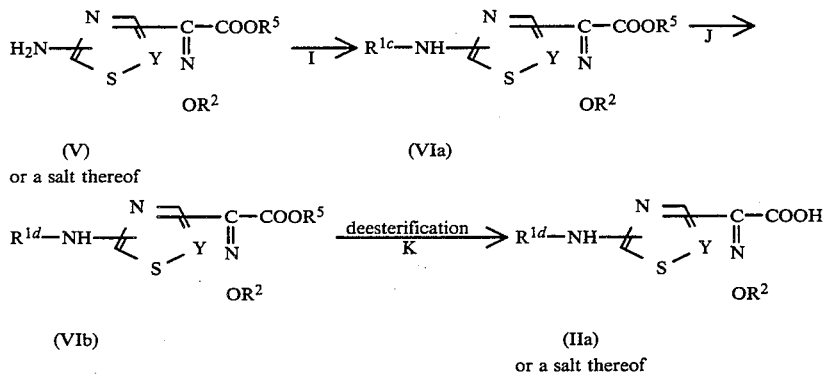

wherein $R^1$, $R^2$ and Y are each as defined above, $R^5$ is an ester moiety of an esterified carboxy represented by a group of the formula: $-COOR^5$, $R^{1c}$ is dihalophosphoryl and $R^{1d}$ is protected phosphono other than dihalophosphoryl.

Further, the compound (III) can be prepared by the following methods.

Preparation

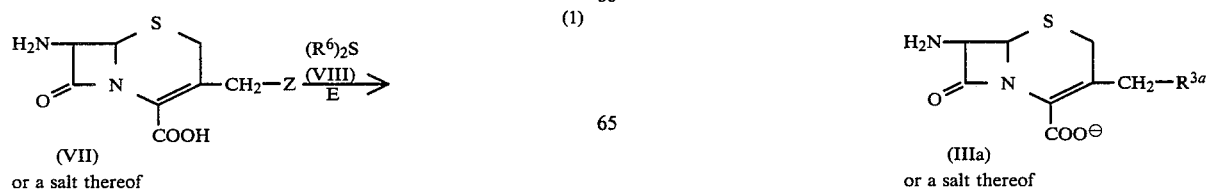

-continued

Preparation

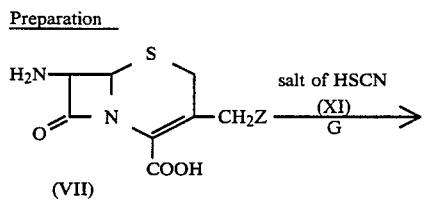
(VII) or a salt thereof

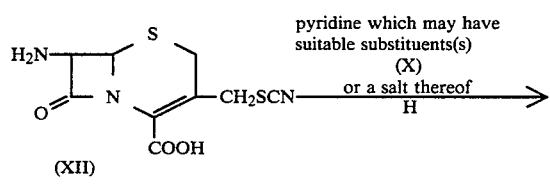
(XII) or a salt thereof

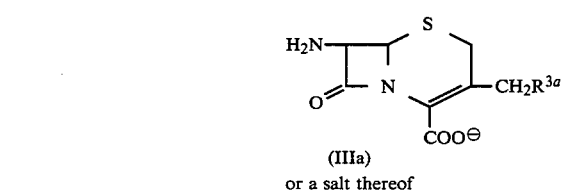
(IIIa) or a salt thereof wherein Z is an acid residue, $R^6$ is lower alkyl and $R^{3a}$ is pyridinio which may have suitable substituent(s).

Regarding the object compounds (I), (Ia), (Ib), (Id) and (Ie) and starting compounds (II), (IIIa), (IV), (V), (VI), (VIa) and (VIb), it is to be understood that said object and starting compounds include syn isomer, anti isomer and a mixture thereof. For example, with regard to the object compound (I), syn isomer means one geometrical isomer having the partial structure represented by the following formula:

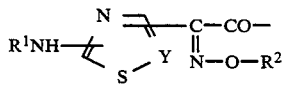

(wherein $R^1$, $R^2$ and Y are each as defined above) and anti isomer means the other geometrical isomer having the partial structure represented by the following formula:

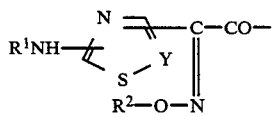

(wherein $R^1$, $R^2$ and Y are each as defined above).

Regarding the other compounds as mentioned above, the syn isomer and the anti isomer can also be referred to the same geometrical isomers as illustrated for the compound (I).

Further, as to the object compounds (I) and (I$_b$), in case that $R^1$ of the compound (I) is phosphono [i.e. the same as the compound (I$_b$)], said compounds (I$_b$) may also be alternatively represented by the formula:

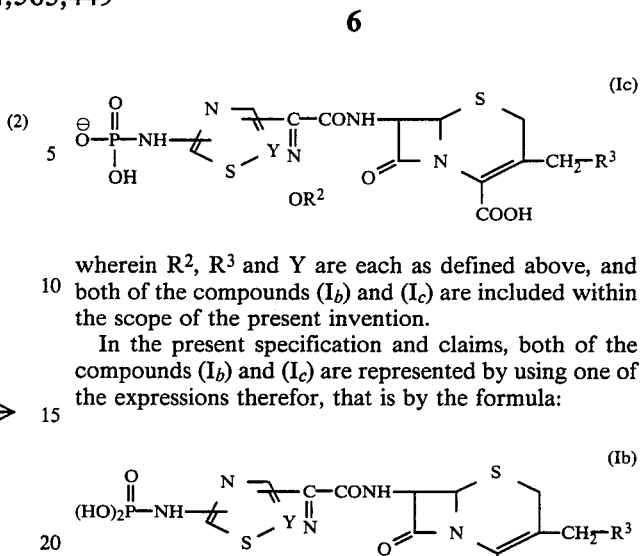

wherein $R^2$, $R^3$ and Y are each as defined above, and both of the compounds (I$_b$) and (I$_c$) are included within the scope of the present invention.

In the present specification and claims, both of the compounds (I$_b$) and (I$_c$) are represented by using one of the expressions therefor, that is by the formula:

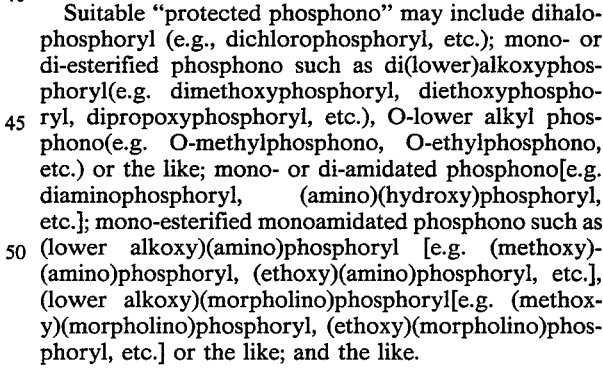

only for the convenient sake.

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "protected phosphono" may include dihalophosphoryl (e.g., dichlorophosphoryl, etc.); mono- or di-esterified phosphono such as di(lower)alkoxyphosphoryl(e.g. dimethoxyphosphoryl, diethoxyphosphoryl, dipropoxyphosphoryl, etc.), O-lower alkyl phosphono(e.g. O-methylphosphono, O-ethylphosphono, etc.) or the like; mono- or di-amidated phosphono[e.g. diaminophosphoryl, (amino)(hydroxy)phosphoryl, etc.]; mono-esterified monoamidated phosphono such as (lower alkoxy)(amino)phosphoryl [e.g. (methoxy)(amino)phosphoryl, (ethoxy)(amino)phosphoryl, etc.], (lower alkoxy)(morpholino)phosphoryl[e.g. (methoxy)(morpholino)phosphoryl, (ethoxy)(morpholino)phosphoryl, etc.] or the like; and the like.

Suitable lower aliphatic hydrocarbon group may include lower alkyl, lower alkenyl, lower alkynyl and the like.

Suitable "lower alkyl" is one having 1 to 6 carbon atom(s) and may include methyl, ethyl, propyl, isopropyl, butyl, isobutyl, tert-butyl, pentyl, tert-pentyl, hexyl and the like, and preferably one having 1 to 4 carbon atom(s).

Suitable "lower alkenyl" is one having 2 to 6 carbon atoms and may include vinyl, allyl, isopropenyl, 1-propenyl, 2-butenyl, 3-pentenyl and the like, and preferably one having 2 to 4 carbon atoms.

Suitable "lower alkynyl" is one having 2 to 6 carbon atoms and may include ethynyl, 2-propynyl, 2-butynyl, 3-pentynyl, 3-hexynyl and the like, and preferably one having 2 to 4 carbon atoms.

Suitable "substituent(s)" on "pyridinio" or "pyridiniothio" may include lower alkyl, halogen, lower alkoxy and the like.

Suitable "halogen" may be chlorine, bromine, iodine or fluorine.

Suitable "lower alkoxy" is one having 1 to 6 carbon atom(s) and may include methoxy, ethoxy, propoxy, isopropoxy, butoxy, t-butoxy, pentyloxy, hexyloxy and the like, and preferably one having 1 to 4 carbon atom(s).

Suitable ester moiety of an esterified carboxy represented by a group of the formula: —COOR$^5$ may be the ones such as lower alkyl ester (e.g. methyl ester, ethyl ester, propyl ester, isopropyl ester, butyl ester, t-butyl ester, pentyl ester, t-pentyl ester, hexyl ester, etc.);

lower alkenyl ester (e.g. vinyl ester, allyl ester, etc.); lower alkynyl ester (e.g. ethynyl ester, propynyl ester, etc.); mono(or di or tri)-halo(lower)alkyl ester (e.g. 2-iodoethyl ester, 2,2,2-trichloroethyl ester, etc.); ar(-lower)alkyl ester, for example, phenyl(lower)alkyl ester which may be substituted with one or more suitable substituent(s) (e.g. benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.); or the like.

Suitable "acid residue" may include acyloxy, halogen as mentioned above, azido and the like.

Suitable "acyloxy" may include lower alkanoyloxy having 1 to 6 carbon atom(s) (e.g. formyloxy, acetoxy, propionyloxy, etc.) and the like, and preferably one having 1 to 3 carbon atom(s).

Suitable "salt of HSCN" may include an alkali metal salt (e.g. sodium salt, potassium salt, etc.), salt with a heavy metal (e.g. cuprous salt, lead salt, etc.), ammonium salt, and the like.

Suitable "dihalophosphoryl" and "protected phosphono other than dihalophosphoryl" can be referred to the ones as exemplified for "protected phosphono".

Preferred embodiments of the object compound (I) are as follows.

Preferred embodiment of R$^1$ is phosphono, di(lower)alkoxyphosphoryl, O-lower alkyl phosphono, diaminophosphoryl, (amino)(hydroxy)phosphoryl or (lower alkoxy)(morpholino)phosphoryl;

R$^2$ is lower alkyl or lower alkenyl;

R$^3$ is a group of the formula:

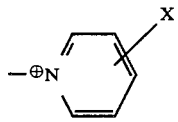

wherein X is hydrogen, halogen or lower alkoxy, or a group of the formula:

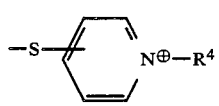

wherein R$^4$ is lower alkyl; and Y is N or CH.

The processes for preparing the object compound (I) are explained in details in the following.

PROCESS 1

The object compound (I) or a salt thereof can be prepared by reacting the compound (II) or its reactive derivative at the carboxy group or a salt thereof with the compound (III) or its reactive derivative at the amino group or a salt thereof.

Suitable reactive derivative at the amino group of the compound (III) may include conventional reactive derivative used in amidation, for example, Schiff's base type imino or its tautomeric enamine type isomer formed by the reaction of the compound (III) with a carbonyl compound; a silyl derivative formed by the reaction of the compound (III) with a silyl compound such as bis(trimethylsilyl)acetamide, trimethylsilylacetamide or the like; a derivative formed by reaction of the compound (III) with phosphorus trichloride or phosgene, and the like.

Suitable salt of the compound (III) may include an acid addition salt such as an organic acid salt (e.g. acetate, maleate, tartrate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative at the carboxy group of the compound (II) may include an acid halide, an acid anhydride, an activated amide, an activated ester, and the like. The suitable example may be an acid chloride; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, acetic acid or trichloroacetic acid, etc.), alkanesulfonic acid (e.g. methanesulfonic acid, ethanesulfonic acid, propanesulfonic acid, etc.) or aromatic carboxylic acid (e.g. benzoic acid, etc.); a symmetrical acid anhydride; an activated amide with imidazole, dimethylpyrazole, triazole or tetrazole; or an activated ester (e.g. cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the compound (II) to be used.

The salts of the compound (II) may be salts with an inorganic base such as an alkali metal salts (e.g. sodium or potassium salt), or an alkaline earth metal salt (e.g. calcium or magnesium salt), a salt with an organic base such as trimethylamine, triethylamine, pyridine, or the like.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, N,N-dimethylacetamide, pyridine or any other organic solvent which does not adversely influence to the reaction. Among these solvents, hydrophilic solvents may be used in a mixture with water.

When the compound (II) is used in free acid form or its salt form in the reaction, the reaction is preferably carried out in the presence of a conventional condensing agent such as N,N-dicyclohexylcarbodiimide; N-cyclohexyl-N'-morpholinoethylcarbodiimide; N-cyclohexyl-N'-(4-diethylaminocyclohexyl)carbodiimide; N,N-diethylcarbodiimide; N,N-diisopropylcarbodiimide; N-ethyl-N'-(3-dimethylaminopropyl)carbodiimide; N,N-carbonylbis(2-methylimidazole); pentamethylene-ketene-N-cyclohexylimine; diphenylketene-N-cyclohexylimine; ethoxyacetylene; ethyl polyphosphate; isopropyl polyphosphate; diethyl phosphorochloridite; phosphorus oxychloride; phosphorus trichloride; phosphorus pentachloride; thionyl chloride; oxalyl chloride; triphenylphosphine; N-ethyl-7-hydroxybenzisoxazolium fluoroborate; N-ethyl-5-phenylisoxazolium-3'-sulfonate; 1-(p-chlorobenzenesulfonyloxy)-6-chloro-1H-benzotriazole; so-called Vilsmeier reagent, for example (chloromethylene) dimethylammonium chloride produced by the reaction of dimethylformamide with thionyl chloride or phosgene, a compound produced by the reaction of dimethylformamide with phosphorus oxychloride, etc.; or the like.

The reaction may be also carried out in the presence of an inorganic or an organic base such as an alkali metal hydroxide, an alkali metal bicarbonate, alkali metal carbonate, alkali metal acetate, tri(lower)-alkylamine, pyridine, N-(lower)alkylmorpholine, N,N-di(lower)alkylbenzylamine, N,N-di(lower)alkylaniline as exemplified below, or the like. When the base or the condensing agent is in liquid, it can be used also as a solvent. The reaction temperature is not critical, and the reaction is usually carried out under cooling or at ambient temperature.

In the present reaction, a syn-isomer of the object compound (I) can be obtained preferably by conducting the reaction of the compound (III) with a syn isomer of the starting compound (II), and "protected phosphono group" for $R^1$, especially dihalophosphoryl, of the compound (II) may be converted into "phosphono" during the reaction or post-treatment of the reaction to give the compound (I) wherein $R^1$ is phosphono, which is also included within the scope of the present reaction.

PROCESS 2

The comound (Ib) or a salt thereof can be prepared by subjecting the compound (Ia) or a salt thereof to elimination reaction of protective group of phosphono.

Suitable salt of the compound (Ia) or (Ib) may be the ones as exemplified for the compound (I).

This elimination reaction can be conducted, for example, by reacting a compound (Ia) or a salt thereof with a trialkylsilyl halide (e.g. trimethylsilyl bromide, trimethylsilyl iodide, trimethylsilyl chloride, etc.), alkali metal halide (e.g. sodium iodide, potassium iodide, sodium bromide, etc.), alkali metal thiocyanate (e.g. sodium thiocyanate, potassium thiocyanate, etc.), or the like.

The reaction is preferably carried out in a solvent such as methylene chloride, dimethylacetamide or any other organic ones which do not adversely influence the reaction. The reaction temperature is not critical and the reaction is usually carried out under relatively mild conditions such as under cooling, at ambient temperature or slightly elevated temperature.

PROCESS 3

The compound (Ie) or a salt thereof can be prepared by subjecting the compound (Id) or a salt thereof to hydrolysis.

The present hydrolysis reaction may include a method using an acid and the like.

Suitable acid may include an organic or an inorganic acid, for example, formic acid, sulfuric acid, trifluoroacetic acid, benzenesulfonic acid, nitric acid, p-toluenesulfonic acid, hydrochloric acid and the like, and preferable acid is, for example, formic acid, trifluoroacetic acid, hydrochloric acid, etc. The acid suitable for the reaction can be selected according to the kind of group to be hydrolyzed.

The present reaction can be carried out in the presence or absence of a solvent. Suitable solvent may include a conventional organic solvent, water or a mixture thereof. When trifluoroacetic acid is used, the elimination reaction may preferably be carried out in the presence of anisole.

The preparations for preparing the starting compound (II) are explained in detail in the following.

PREPARATION A

The compound (V) or a salt thereof can be prepared by subjecting the compound (IV) or its reactive derivative at the carboxy group or a salt thereof to esterification.

Suitable salt of the compound (IV) can be referred to the ones as exemplified for the compound (III), and salt of the compound (V) may include acid addition salt as exemplified for the compound (III).

Suitable reactive derivative at the carboxy group of the compound (IV) can be referred to the ones as exemplified for the compound (II).

The esterifying agent to be used in the present esterification reaction may include the compound represented by the formula:

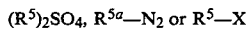

wherein $R^5$ is as defined above, $R^{5a}$ is a group in which a hydrogen is eliminated from $R^5$ and X is hydroxy or halogen.

Suitable halogen may include chlorine, bromine, iodine or fluorine.

The reaction using the esterifying agent represented by the formula: $(R^5)_2SO_4$ or $R^5-X$ is usually carried out in a solvent such as water, acetone, methylene chloride, ethanol, ether, dimethylformamide or any other solvent which does not adversely influence the reaction.

The present reaction is preferably carried out in the presence of a base such as an inorganic base or an organic base as aforementioned.

The reaction remperature is not critical and the reaction is usually carried out under cooling to heating around boiling point of the solvent.

The reaction using the esterifying agent represented by the formula: $R^{5a}-N_2$ is usually carried out in a solvent such as ether, tetrahydrofuran or the like.

The reaction temperature is not critical and the reaction is usually carried out under cooling or at ambient temperature.

PREPARATIONS B AND D

The compound (VI) or the compound (II) or its reactive derivative at the carboxy group or a salt thereof can be prepared by subjecting the compound (V) or a salt thereof or the compound (IV) or its reactive derivative at the carboxy group or a salt thereof to introduction reaction of phosphono or protected phosphono on amino, respectively.

Suitable reactive derivative at the carboxy group of the compound (IV) can be referred to the ones as exemplified for the compound (II).

Suitable agent to be used in the present introduction reaction may include phosphorus halide (e.g. phosphorus trichloride, phosphorus pentachloride, etc.), phosphorus oxychloride and the like.

The present reaction is usually carried out in a solvent such as alkylene halide (e.g. methylene chloride, ethylene chloride, etc.), toluene or the like.

The reaction temperature is not critical and the reaction is usually carried out under cooling, at ambient temperature or under warming.

In the present reaction, the reaction mixture obtained by reacting the compound (IV) or (V) with the agent as above (e.g. phosphorus halide, etc.) wherein $R^1$ may be dihalophosphoryl may be further treated with water to give the compound (II) or (IV) wherein $R^1$ is phosphone, and the same reaction mixture may be further treated with alcohol such as alkanol (e.g. methanol, ethanol, etc.) or the like to give the compound (II) or (VI) wherein $R^1$ is esterified phosphono. Of course, the reaction product of the compound (II) or (VI) wherein $R^1$ is dihalophosphoryl can be obtained from the reaction mixture as stated above by a conventional isolation method and it can be used in the next step reaction.

The present reaction includes, within its scope, the case that the carboxy group of the compound (IV) is converted into its reactive derivative during the reaction.

PREPARATION C

The compound (II) or a salt thereof can be prepared by subjecting the compound (VI) to deesterification reaction.

Suitable salt of the compound (II) can be referred to the ones as exemplified for the compound (I).

The present reaction is carried out in accordance with a conventional method such as hydrolysis, reduction or the like. Hydrolysis is preferably carried out in the presence of a base or an acid. Suitable base may include an inorganic base and an organic base such as an alkali metal (e.g. sodium, potassium, etc.), an alkaline earth metal (e.g. magnesium, calcium etc.), the hydroxide or carbonate or bicarbonate thereof, trialkylamine (e.g. trimethylamine, triethylamine, etc.), picoline, 1,5-diazabicyclo[4,3,0]non-5-ene, 1,4-diazabicyclo[2,2,2]octane, 1,8-diazabicyclo[5,4,0]undecene-7, or the like. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.). Trifluoroacetic acid is preferably used in the presence of a cation trapping agent (e.g. anisole, etc.).

The reaction is usually carried out in a solvent such as water, methylene chloride, tetrahydrofuran, an alcohol (e.g. methanol, ethanol, etc.), a mixture thereof or any other solvent which does not adversely influence to the reaction. A liquid base or acid can be also used as the solvent. The reaction temperature is not critical and the reaction is usually carried out under cooling to warming.

Reduction can be applied preferably for elimination of ester moiety such as 4-nitrobenzyl, 2-iodoethyl, 2,2,2-trichloroethyl, or the like. The reduction method applicable for the deesterification reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

The preparations for preparing the starting compound (IIa) are explained in detail in the following.

PREPARATION I

The compound (VIa) can be prepared by subjecting the compound (V) or a salt thereof to introduction reaction of dihalophosphoryl on amino.

The present reaction can be carried out according to similar manners to those of Preparations B and D.

PREPARATION J

The compound (VIb) can be prepared by subjecting the compound (VIa) to conversion reaction of "dihalophosphoryl" to "protected phosphono other than dihalophosphoryl".

The present conversion reaction can be carried out by subjecting the compound (VIa) to esterification and/or amidation.

The present esterification reaction can be conducted by reacting the compound (VIa) with an alcohol.

Suitable alcohol may include an alkanol (e.g. methanol, ethanol, propanol, butanol, etc.) and the like.

The amidation reaction can be conducted by reacting the compound (IVa) with an amine.

Suitable amine may include ammonia, primary amine (e.g. methylamine, ethylamine, etc.), secondary amine (e.g. morpholin, dimethylamine, etc.) and the like.

The present esterification or amidation reaction is usually carried out in a solvent such as alkylene halide (e.g. methylene chloride, ethylene chloride, etc.), tetrahydrofuran, water or any other solvent which does not adversely affect the reaction.

The reaction temperature is not critical and the reaction is usually carried out under cooling or at ambient temperature.

PREPARATION K

The compound (IIa) or a salt thereof can be prepared by subjecting the compound (VIb) to deesterification reaction.

The present deesterification reaction can be carried out according to a similar manner to that of Preparation C.

The Preparations for preparing the starting compound (IIIa) are explained in detail in the following.

PREPARATIONS E AND G

The compound (IX) or a salt thereof or the compound (XII) or a salt thereof can be prepared by reacting the compound (VII) or a salt thereof with the compound (VIII) or with the salt of the compound (XI), respectively.

Suitable salt of the compounds (VII), (IX) and (XII) can be referred to the ones as exemplified for the compound (III).

The present reaction is usually carried out in a solvent such as alkanoic acid (e.g. acetic acid, trifluoroacetic acid, etc.), dimethylformamide, nitromethane, acetonitrile or any other solvent which does not adversely affect the reaction.

The present reaction is preferably carried out in the presence of sulfonic acid (e.g., trifluoromethanesulfonic acid, chlorosulfonic acid, etc.) and the like.

The reaction temperature is not critical and the reaction is usually carried out under cooling to ambient temperature.

PREPARATIONS F AND H

The compounds (IIIa) or a salt thereof can be prepared by reacting the compound (IX) or a salt thereof or the compound (XII) or a salt thereof with the compound (X) or a salt thereof, respectively.

Suitable salt of the compound (IX) and (XII) can be referred to the ones exemplified for the compound (III).

Suitable salt of the compound (X) may include an acid addition salt as exemplified for the compound (III).

The present reaction may be carried out in a solvent such as water, phosphate buffer, acetone, chloroform, acetonitrile, nitrobenzene, methylene chloride, ethylene chloride, formamide, dimethylformamide, methanol, ethanol, ether, tetrahydrofuran, dimethylsulfoxide, or any other organic solvent which does not adversely affect the reaction. Among the solvents, hydrophilic solvents may be used in a mixture with water. The reaction is preferably carried out in around neutral medium. When the compound (IX) or (XII) is used in acid salt form, the reaction may be conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out under cooling, at ambient temperature, under warming or under heating.

Thus obtained compounds according to Processes 1 to 3 as above may be converted into pharmaceutically acceptable salts thereof by conventional manner.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention may be effective for treating of infectious diseases caused by a number of pathogenic bacteria. In general amounts, daily dose between 1 mg/body and about 1000 mg/body or even more may be administered.

The object compound (I) of the present invention is characterized by possessing higher solubility in water as compared with the corresponding free aminothiadiazolyl or thiazolyl compound (i.e., $R^1$—NH means amino), which is slightly soluble in water, and by possessing a feature that $R^1$ group can be split under physiological conditions to give the corresponding free aminothiadiazolyl or thiazolyl compound.

Accordingly, the object of the present invention is to provide a more soluble form of the corresponding aminothiadiazolyl or aminothiazolyl compound which is slightly soluble in water.

Now in order to show the utility of the object compounds (I), test data on anti-microbial activity of a representative compound of the present invention are shown below.

TEST METHOD

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of $\mu g/ml$ after incubation at 37° C. for 20 hours.

TEST COMPOUND

7-[2-Allyloxyimino-2-(5-phosphonoamino-1,2,4-thiadiazol-3-yl)acetamido]-3-(1-pyridiniomethyl)-3-cephem-4-carboxylate (syn isomer)

TEST RESULTS

| Test Bacteria | M.I.C. ($\mu g/ml$) |
|---|---|
| E. coli 31 | 0.78 |

The following Preparations and Examples are given for the purpose of illustrating the present invention.

PREPARATION 1

To a solution of 2-allyloxyimino-2-(5-amino-1,2,4-thiadiazol-3-yl)acetic acid (syn isomer) (10 g) in tetrahydrofuran (230 ml) was added portionwise diphenyldiazomethane (12.76 g) under cooling in an ice bath and stirring and the mixture was stirred for 2 hours at room temperature. The resulting mixture was concentrated under reduced pressure until an crystallization began and stood overnight at room temperature. The precipitates were collected by filtration, washed with ethyl acetate and dried to give diphenylmethyl 2-allyloxyimino-2-(5-amino-1,2,4-thiadiazol-3-yl)acetate (syn isomer) (5.41 g), mp. 175° to 180° C. (dec.). The filtrate and the washings were combined and evaporated to dryness. The residue was crystallized from methylene chloride-diethyl ether (4:1) to give further crops of the object compound (6.7 g), which was recrystallized from acetonitrile.

IR (Nujol): 3460, 1730, 1620, 1530, 1260, 1150, 1015 cm$^{-1}$.

NMR (DMSO-d$_6$, $\delta$): 4.71 (2H, d, J=5 Hz), 5.05–5.50 (2H, m), 5.65–6.30 (1H, m), 7.06 (1H, s), 7.40 (10H, s), 8.22 (2H, broad s).

PREPARATION 2

To a cold solution of phosphorus pentachloride (3.74 g) in methylene chloride (43 ml) was added diphenylmethyl 2-allyloxyimino-2-(5-amino-1,2,4-thiadiazol-3-yl)acetate (syn isomer) (3.94 g) at −20° C. under stirring. To the mixture was added dropwise pyridine (2.37 g) under cooling below −22° C. in a dry ice-acetone bath and stirring, which was continued for one hour at −9° to −5° C. in an ice-salt bath. After the mixture was cooled to −35° C. and pyridine (6.16 g) was added thereto, a solution of methanol (5.5 ml) in methylene chloride (36 ml) was added dropwise to the mixture below −12° C. The mixture was stirred for 10 minutes at −10° to 0° C. and for additional 10 minutes at 0° to 15° C. Cold water (70 ml) was added to the reaction mixture and the organic layer was separated out, washed with water (100 ml) and a saturated aqueous solution of sodium chloride and then evaporated. The residual oil was subjected to column chromatography on silica gel (140 g) using benzene/ethyl acetate (2/1–½) as eluents. The fractions containing the object compound were combined and evaporated to give diphenylmethyl 2-allyloxyimino-2-[5-dimethoxyphosphorylamino-1,2,4-thiadiazol-3-yl]acetate (syn isomer) (2.90 g) as an oil.

It crystallized by allowing to stand in a refrigerator, mp. 91° to 95° C.

IR (Film): 3500, 3100-2800, 1750, 1590, 1530, 1450, 1390, 1280-1230, 1185, 1115, 1070-1010 cm$^{-1}$.

NMR (DMSO-d$_6$, δ): 3.75 (6H, d, J=12 Hz), 4.75 (2H, d, J=5 Hz), 5.0-5.5 (2H, m), 5.65-6.26 (1H, m), 7.07 (1H, s), 7.37 (10H, s).

Analysis for $C_{22}H_{23}N_4O_6P$: Calc'd.: C: 52.59, H: 4.61, N: 11.15. Found: C: 52.44, H: 4.83, N: 10.79.

PREPARATION 3

To a solution of diphenylmethyl 2-allyloxyimino-2-[5-dimethoxyphosphorylamino-1,2,4-thiadiazol-3-yl]acetate (syn isomer) (4.0 g) and anisole (10 ml) in methylene chloride (10 ml) was added dropwise trifluoroacetic acid (22 ml) below −2° C. under cooling in an ice-salt bath and stirring, which was continued for 20 minutes at −8° to −2° C. The reaction mixture was evaporated under reduced pressure and the residual oil was dissolved in a mixture of ethyl acetate (60 ml) and water (50 ml), adjusting to pH 6 with aqueous sodium bicarbonate. The aqueous layer was separated out and adjusted to pH 1 with 6N-hydrochloric acid under an addition of ethyl acetate (60 ml). The organic layer was separated out and the aqueous layer was extracted with ethyl acetate. The organic layer and the extract were combined, washed with a saturated aqueous solution of sodium chloride, dried over magnesium sulfate and evaporated to dryness. To the residue dissolved in ethyl acetate (8 ml) were added a solution of sodium acetate (0.98 g) in methanol (25 ml) and the mixture was evaporated to dryness. The residue was triturated in diisopropyl ether to give sodium 2-allyloxyimino-2-[5-dimethoxyphosphorylamino-1,2,4-thiadiazol-3-yl]acetate (syn isomer) (2.67 g), mp. 131° to 137° C. (dec.).

IR (Nujol): 3420, 3100, 1690, 1670, 1615, 1530 cm$^{-1}$.

NMR (D$_2$O, δ): 3.92 (6H, d, J=12 Hz), 4.80 (2H, m) 5.18-5.70 (2H, m), 5.70-6.48 (1H, m).

PREPARATION 4

The following compound was obtained according to a similar manner to that of Preparation 1. Diphenylmethyl 2-ethoxyimino-2-(5-amino-1,2,4-thiadiazol-3-yl)acetate (syn isomer), mp. 193° to 196.5° C. (dec.).

IR (Nujol): 3460, 1735, 1610, 1530, 1500 cm$^{-1}$.

NMR (DMSO-d$_6$, δ): 1.20 (3H, t, J=7 Hz), 4.23 (2H, q, J=7 Hz), 7.10 (1H, s), 7.3 (10H, m), 8.27 (2H, s).

PREPARATION 5

The following compound was obtained according to a similar manner to that of Preparation 2. Diphenylmethyl 2-ethoxyimino-2-[5-dimethoxyphosphorylamino-1,2,4-thiadiazol-3-yl]acetate (syn isomer), mp. 128° to 130° C.

IR (Nujol): 3070, 1750, 1590, 1530, 1450, 1390, 1250, 1240, 1185, 1140, 1110, 1095, 1060, 1040 cm$^{-1}$.

NMR (DMSO-d$_6$, δ): 1.18 (3H, t, J=7 Hz), 3.68 (6H, d, J=11 Hz), 4.20 (2H, q, J=7 Hz), 7.00 (1H, s), 7.30 (10H, s), 10.6-11.5 (1H, broad s).

PREPARATION 6

The following compound was obtained according to a similar manner to that of Preparation 3. Sodium 2-ethoxyimino-2-[5-dimethoxyphosphorylamino-1,2,4-thiadiazol-3-yl]acetate (syn isomer), mp. 142° to 1,2,4-thiadiazol-3-yl]acetate (syn isomer), mp. 142° to 148.5° C. (dec.).

IR (Nujol): 3500, 3430, 2700, 1670, 1610, 1530, 1400, 1280, 1270, 1180, 1145, 1110, 1050, 1030 cm$^{-1}$.

NMR (D$_2$O, δ): 1.34 (3H, t, J=7 Hz), 3.90 (6H, d, J=12 Hz), 4.31 (2H, q, J=7 Hz).

EXAMPLE 1

To a suspension of sodium 2-allyloxyimino-2-[5-dimethoxyphosphorylamino-1,2,4-thiadiazol-3-yl]acetate (syn isomer) (358.5 mg) and sodium bicarbonate (42 mg) in N,N-dimethylacetamide (3.6 ml) was added dropwise methanesulfonyl chloride (172 mg) under cooling in an ice bath and stirring, which was continued for 1.5 hours at the same temperature. On the other hand, a mixture of 7-amino-3-(1-pyridiniomethyl)-3-cephem-4-carboxylate dihydrochloride (400 mg) and trimethylsilylacetamide (2 g) in methylene chloride (4 ml) was stirred at room temperature to give a solution and cooled to −30° C. The cold solution was added to the activated mixture prepared above and the resulting mixture was stirred for 30 minutes at −20° to −15° C. and then for additional 20 minutes at −15° to 0° C. The mixture was poured into 6% aqueous solution of sodium bicarbonate (5 ml), adjusted to pH 3 with 6N hydrochloric acid and evaporated to remove methylene chloride. The residual aqueous solution was diluted to 72 ml with water and subjected to column chromatography on a nonionic adsorption resin "Diaion HP-20" (Trademark: prepared by Mitsubishi Chemical Industries) (36 ml). After the column was washed with water, the elution was carried out with 30% and 40% aqueous methanol successively. The fractions containing the object compound were collected, evaporated to remove methanol under reduced pressure and lyophilized to give 7-[2-allyloxyimino-2-{5-dimethoxyphosphorylamino-1,2,4-thiadiazol-3-yl}acetamido]-3-(1-pyridiniomethyl)-3-cephem-4-carboxylate (syn isomer) 379 mg), mp. 157° to 165° C. (dec.).

IR (Nujol): 3350, 3200, 1770, 1670, 1610, 1520 cm$^{-1}$.

NMR (DMSO-d$_6$+D$_2$O, 67 ): 3.12 and 3.50 (2H, ABq, J=18 Hz), 3.67 (6H, d, J=11 Hz), 4.65 (2H, m), 5.0-6.0 (5H, m), 5.08 (1H, d, J=5 Hz), 5.72 (1H, d, J=5 Hz), 8.17 (2H, m), 8.53 (1H, m), 9.35 (2H, m).

EXAMPLE 2

To a solution of phosphorus pentachloride (4.99 g) in methylene chloride (60 ml) was added 2ethoxyimino-2-

(5amino-1,2,4-thiadiazol-3-yl)acetyl chloride monohydrochloride (syn isomer) (5.42 g) under cooling in an ice bath and stirring, which was continued for one hour at room temperature. The mixture was evaporated to dryness and the residue was dissolved in acetone (30 ml). The solution was added dropwise to a solution of 7-amino-3-(1-pyridiniomethyl)-3-cephem-4-carboxylate dihydrochloride (5.42 g) in 40% aqueous acetone (50 ml) under cooling in an ice bath and stirring, adjusting to pH 6.5 with aqueous sodium bicarbonate during the addition. After stirring for one hour in an ice bath, acetone was removed by evaporation and the remaining aqueous solution was adjusted to pH 1 with 6N hydrochloric acid. The resulting insoluble material was removed by filtration and the filtrate was subjected to column chromatography on a non ionic adsorption resin "Diaion HP-20" (540 ml). The elution was carried out with water, 5%, 10% and 20% aqueous methanol successively. The fractions containing an object compound were collected and concentrated to 10 ml under reduced pressure. The residual solution was poured into acetone (200 ml) under stirring and the resulting precipitates were collected by filtration and dried to give 7-[2-ethoxyimino-2-(5-phosphonoamino-1,2,4-thiadiazol-3-yl)acetamido]-3-(1-pyridiniomethyl)-3-cephem-4-carboxylate (2.59 g), mp. 165° to 173° C. (dec.).

IR (Nujol): 3200, 2350, 1780, 1670, 1630, 1510 cm$^{-1}$.

NMR (DMSO-d$_6$+D$_2$O, δ): 1.19 (3H, t, J=7 Hz), 3.1–3.7 (2H, m), 3.9–4.5 (2H, m), 5.23 (1H, d, J=5 Hz), 5.0–6.1 (2H, m), 5.91 (1H, d, J=5 Hz), 8.26 (2H, m), 8.65 (1H, m), 9.18 (2H, m).

EXAMPLE 3

To a solution of 7-[2allyloxyimino-2-{5-dimethoxyphosphorylamino-1,2,4-thiadiazol-3-yl}acetamido]-3-(1-pyridiniomethyl)-3-cephem-4-carboxylate (syn isomer) in the reaction mixture prepared from sodium 2allyloxyimino-2-[5-dimethoxyphosphorylamino-1,2,4-thiadiazol-3-yl]acetate (syn isomer) (502 mg) and 7-amino-3-(1-pyridiniomethyl)-3-cephem-4-carboxylate dihydrochloride (560 mg) according to a similar procedure to that of Example 1 was added dropwise trimethylsilyl bromide (3.22 g) under cooling in an ice bath and stirring, which was continued for one hour at room temperature. To the mixture was added acetic acid (0.5 ml) and the mixture was poured into diisopropyl ether (500 ml) under stirring. The resulting oily product was separated out by decantation and dissolved in water (50 ml). The aqueous solution was subjected to column chromatography on a non ionic adsorption resin "Diaion HP-20" (50 ml). The elution was carried out with water and 10% aqueous methanol. The fractions containing the object compound were collected, evaporated to remove methanol under reduced pressure and lyophilized to give 7-[2-allyloxyimino-2-(5-phosphonoamino-1,2,4-thiadiazol-3-yl)acetamido]-3-(1-pyridiniomethyl)-3-cephem-4-carboxylate (syn isomer) (250 mg), mp. 175° to 181° C. (dec.).

IR (Nujol): 3200, 2350, 1780, 1670, 1630, 1520 cm$^{-1}$.

NMR (DMSO-d$_6$+D$_2$O, δ): 3.51 (2H, m), 4.72 (2H, m), 5.06–6.30 (5H, m), 5.23 (1H, d, J=5 Hz), 5.92 (1H, d, J=5 Hz), 8.27 (1H, m), 8.70 (1H, m), 9.13 (2H, m).

EXAMPLE 4

The following compound was obtained according to similar manners to those of Examples 1 to 3. 7-[2-Ethoxyimino-2-(5-phosphonoamino-1,2,4-thiadiazol-3-yl)acetamido]-3-(1-methyl-4-pyridiniothiomethyl)-3-cephem-4-carboxylate (syn isomer), mp. 160° to 169° C. (dec.).

IR (Nujol): 3250, 1770, 1670, 1630, 1520 cm$^{-1}$.

NMR (DMSO-d$_6$+D$_2$O, δ): 1.24 (3H, t, J=7 Hz), 3.70 (2H, m), 4.22 (3H, s), 4.35 (4H, m), 5.21 (1H, d, J=5 Hz), 5.83 (1H, d, J=5 Hz), 7.95 (2H, d, J=7 Hz), 8.62 (2H, d, J=7 Hz).

PREPARATION 7

To a suspension of phosphorus pentachloride (243.36 g) in toluene (2.5 l) was added 2-allyloxyimino-2-(5-amino-1,2,4-thiadiazol-3-yl)acetic acid (syn isomer) (102.6 g) under cooling at 0° C. and stirring, which was continued for 45 minutes at 4° to 8° C. The reaction mixture was poured into ice-cold water (1.5 l) under stirring. The organic layer was separated out, washed with cold water (2 l) and brine (1 l), dried over magnesium sulfate and evaporated to dryness. The residue was triturated in diisopropyl ether (150 ml) and the mixture was stirred for 10 minutes at 3° C. The resulting precipitate was filtered, washed with cold diisopropyl ether (50 ml) and dried to give 2-allyloxyimino-2-(5-dichlorophosphorylamino-1,2,4-thiadiazol-3-yl)acetyl chloride (syn isomer) (128.7 g).

mp. 128° to 129° C.

IR (Nujol): 1798, 1774, 1585, 1250, 1125, 1040, 985 cm$^{-1}$.

PREPARATION 8

The following compounds were obtained according to a similar manner to that of Preparation 7.

(1) 2-Ethoxyimino-2-(5-dichlorophosphorylamino-1,2,4-thiadiazol-3-yl)acetyl chloride (syn isomer), mp. 115° C.

IR (Nujol): 1780, 1590, 1530, 1220, 1050, 960, 910 cm$^{-1}$.

NMR (d$_6$-acetone, δ): 1.37 (3H, t, J=7 Hz), 4.45 (2H, q, J=7 Hz).

Analysis for C$_6$H$_6$N$_4$O$_3$PSCl$_3$

|  | C | H | N | Cl | P |
|---|---|---|---|---|---|
| calc'd: | 20.48 | 1.71 | 15.93 | 30.33 | 8.82 |
| found: | 20.79 | 1.78 | 16.22 | 30.63 | 8.98 |

(2) 2-Propoxyimino-2-(5-dichlorophosphorylamino-1,2,4-thiadiazol-3-yl)acetyl chloride (syn isomer), mp. 127° to 130° C.

IR (Nujol): 1790, 1590, 1530, 1220, 1120, 1050, 1010, 940 cm$^{-1}$.

PREPARATION 9

To solution of phosphorus pentachloride (10.92 g) in methylene chloride (110 ml) was added 2-allyloxyimino-2-(5-amino-1,2,4-thiadiazol-3-yl)acetic acid (syn isomer) (11.4 g) under cooling at −20° C. and stirring, which was continued for 50 minutes at −15° to −5° C. To the mixture was dropped a solution of methanol (2.4 g) in pyridine (15.82 g) at −30° to −10° C. under stirring, which was continued for 20 minutes at −10° C. To the reaction mixture was dropped water (110 ml) and the mixture was adjusted to pH 2 with 1N aqueous sodium hydroxide and then stirred for 30 minutes at 0° C. The resulting precipitate was filtered, washed with water and dried to give methyl 2-allyloxyimino-2-(5- amino-1,2,4-thiadiazol-3-yl)acetate (syn isomer) (8.40 g).

mp. 167° to 168° C.

IR (Nujol): 3425, 3260, 3140, 1745, 1625, 1600, 1540, 1440, 1410, 1290, 1145, 1075, 1015, 995 cm$^{-1}$.

NMR (d$_6$-DMSO, δ): 3.83 (3H, s), 4.7 (2H, m), 5.0–5.5 (2H, m), 5.7–6.3 (1H, m), 8.25 (2H, s).

PREPARATION 10

To a mixture of phosphorus pentachloride (65.4 g) and pyridine (37.3 g) in methylene chloride (654 ml) was added methyl 2-allyloxyimino-2-(5-amino-1,2,4-thiadiazol-3-yl)acetate (syn isomer) (38.1 g) under cooling at −15° C. and stirring, which was continued for 30 minutes at −10° to −5° C. To the reaction mixture was added water (300 ml) at −10° to 5° C. and the organic layer was separated out, washed with water, dried over magnesium sulfate and filtered. The filtrate was added to a solution of methanol (25.1 g) and pyridine (149 g) in methylene chloride (785 ml) at −20° to −10° C. under stirring, which was continued for 30 minutes at −10° to −5° C. and 4 hours at ambient temperature. The mixture was diluted with water (1 l) and adjusted to pH 1.0 with 6N hydrochloric acid. The organic layer was separated out, washed with water, dried over magnesium sulfate and evaporated to dryness. The residue was triturated in diethyl ether to give methyl 2-allyloxyimino-2-(5-dimethoxyphosphorylamino-1,2,4-thiadiazol-3-yl)acetate (syn isomer) (38.7 g).

mp. 113° to 114° C.

IR (Nujol): 3080, 1745, 1595, 1535, 1430, 1390, 1270, 1250, 1230, 1110, 1030 cm$^{-1}$.

NMR (d$_6$-DMSO, δ): 3.73 (6H, d, J=12 Hz), 3.87 (3H, s), 4.7–5.0 (2H, m), 5.1–5.5 (2H, m), 5.7–6.3 (1H, m).

PREPARATION 11

To a solution of methyl 2-allyloxyimino-2-(5-dimethoxyphosphorylamino-1,2,4-thiadiazol-3-yl)acetate (syn isomer) (37.3 g) in tetrahydrofuran (106 ml) was added 1N-aqueous sodium hydroxide (234 ml) and the mixture was stirred for 2 hours at ambient temperature. The reaction mixture was adjusted to pH 5 with 6N hydrochloric acid and washed with ethyl acetate. The aqueous layer was separated out, adjusted to pH 1.0 with 6N hydrochloric acid and extracted with ethyl acetate. The extract was washed with brine, dried over magnesium sulfate and evaporated. The residue dissolved in methanol (50 ml) was added dropwise to a solution of sodium acetate (8.7 g) in methanol (90 ml) at ambient temperature under stirring, which was continued for one hour at the same temperature. To the mixture was added ethyl acetate (200 ml) and the resulting precipitate was collected by filtration, washed with ethyl acetate and dried to give sodium 2-allyloxyimino-2-(5-dimethoxyphosphorylamino-1,2,4-thiadiazol-3-yl)acetate (syn isomer) (32.6 g), mp. 168° to 173° C. (dec).

IR (Nujol): 3450, 1590, 1535, 1395, 1270, 1190, 1130, 1050, 1025, 945, 845 cm$^{-1}$.

NMR (d$_6$-DMSO, δ): 3.65 (6H, d, J=12 Hz), 4.5–4.8 (2H, m) 5.0–5.6 (2H, m), 5.7–6.4 (1H, m).

PREPARATION 12

The following compound was obtained according to similar manners to those of Preparations 2 and 10. Ethyl 2-methoxyimino-2-(2-dimethoxyphosphorylaminothiazol-4-yl)acetate (syn isomer), oil.

IR (Film): 3480, 3120, 3000, 2950, 2900, 1740, 1630, 1580, 1530, 1465, 1450, 1375, 1290–1240, 1200–1170, 1170–1020, 970, 920, 850, 785 cm$^{-1}$.

NMR (DMSO-d$_6$, δ): 1.30 (3H, t, J=7 Hz), 3.72 (6H, d, J=12 Hz), 3.92 (3H, s), 4.33 (2H, q, J=7 Hz), 7.34 (1H, s), 10.29 (1H, broad s).

PREPARATION 13

The following compound was obtained according to similar manners to those of Preparations 3 and 11. Sodium 2-methoxyimino-2-(2-dimethoxyphosphorylaminothiazol-4-yl)acetate (syn isomer), mp. 152° to 160° C. (dec.).

IR (Nujol): 1620, 1545, 1400, 1275, 1185, 1045 cm$^{-1}$.

NMR (D$_2$O, δ): 3.79 (6H, d, J=11 Hz), 3.91 (3H, s) 7.07 (1H, s).

PREPARATION 14

To a mixture of 7-(2-thienylacetamido)-3-(3-chloro-1-pyridiniomethyl)-3-cephem-4-carboxylate (22.5 g) and N,N-dimethylaniline (60.0 g) in methylene chloride (400 ml) was added dropwise trimethylsilylchloride (50.0 g) at ambient temperature under stirring, which was continued for 15 minutes at the same temperature. The reaction mixture was cooled to −30° C. and phosphorus pentachloride (31.2 g) was added thereto under stirring, which was continued for one hour at −30° to −25° C. The reaction mixture was added to a cold solution of 1,3-butanediol (45 g) in methylene chloride (400 ml) under cooling in an ice-bath and stirring, which was continued for one hour at ambient temperature. The resulting precipitate was filtered, washed with methylene chloride and redissolved in methanol (50 ml). After the solution was treated with activated charcoal (1 g), the filtrate was poured into acetone (500 ml) under stirring, which was continued for 30 minutes at ambient temperature. The resulting precipitate was filtered, washed with acetone and dried to give 7-amino-3-(3-chloro-1-pyridiniomethyl)-3-cephem-4-carboxylate dihydrochloride (17.7 g), mp. 160° to 165° C. (dec.).

IR (Nujol): 3350, 1790, 1720, 1620, 1490, 1170 cm$^{-1}$.

NMR (D$_2$O, δ): 3.50 and 3.80 (2H, ABq, J=18 Hz), 5.28 (1H, d, J=4 Hz), 5.40 (1H, d, J=4 Hz), 5.48 and 5.80 (2H, ABq, J=14 Hz), 8.0–8.3 (1H, m) 9.27–9.57 (3H, m).

PREPARATION 15

The following compound was obtained according to a similar manner to that of Preparation 14. 7-amino-3-(4-methoxy-1-pyridiniomethyl)-3-cephem-4-carboxylate hydrochloride IR (Nujol): 3400, 1780, 1640, 1570, 1525, 1420 cm$^{-1}$.

NMR (D$_2$O, δ): 3.20 and 3.57 (2H, ABq, J=18 Hz), 4.10 (3H, s), 5.00 and 5.20 (2H, ABq, J=14 Hz), 5.20 (1H, d, J=4 Hz), 5.23 (1H, d, J=4 Hz), 7.47 (2H, d, J=7 Hz), 8.67 (2H, d, J=7 Hz).

PREPARATION 16

To a mixture of 7-aminocephalosporanic acid (6.0 g) and dimethyl sulfide (1.36 g) in acetonitrile (30 ml) was added trifluoromethanesulfonic acid (9.0 g) below 18° C. under cooling in an ice-bath and stirring, which was continued for 30 minutes at 15° to 18° C. To the reaction mixture was added ethyl acetate (80 ml), and the mixture was seeded and stirred for one hour at ambient temperature. A resulting precipitate was filtered, washed with ethyl acetate and dried to give 7-amino-3- dimethylsulfoniomethyl-3-cephem-4-carboxylate bis(trifluoromethanesulfonate) (8.55 g), mp. 190° to 195° C. (dec.).

IR (Nujol): 3150, 3000, 1790, 1700, 1635, 1600, 1490, 1420, 1220, 1160, 1020 cm$^{-1}$.

NMR (D$_2$O, δ): 3.00 (6H, s), 3.67 and 3.87 (2H, ABq, J=18 Hz), 4.53 (2H, broad s), 5.20 (1H, d, J=4 Hz) 5.33 (1H, d, J=4 Hz).

Analysis for C$_{12}$H$_{16}$N$_2$O$_9$S$_4$F$_6$:

|  | C | H | N | S | F |
| --- | --- | --- | --- | --- | --- |
| calc'd: | 25.09 | 2.81 | 4.88 | 22.32 | 19.84 |
| found: | 25.11 | 2.78 | 5.04 | 22.93 | 20.23 |

PREPARATION 17

To a solution of 7-amino-3-dimethylsulfoniomethyl-3-cephem-4-carboxylate bis(trifluoromethanesulfonate) (574.5 mg) in N,N-dimethylformamide (10 ml) was added pyridine (395 mg) under cooling in an ice-bath and stirring, which was continued for 30 minutes at 0° to 5° C. The reaction mixture was diluted with water to 50 ml and the solution was subjected to H.P.L.C. to identify the reaction product and calculate the yield. It contained 7-amino-3-(1-pyridiniomethyl)-3-cephem-4-carboxylate (133.5 mg).

PREPARATION 18

To a mixture of 7-aminocephalosporanic acid (45.0 g) and potassium thiocyanate (14.55 g) in acetonitrile (225 ml) was added dropwise trifluoromethanesulfonic acid (67.5 g) below 18° C. under cooling in an ice-bath and stirring, which was continued for 30 minutes at 15° to 18° C. The reaction mixture containing 7-amino-3-cyanothiomethyl-3-cephem-4-carboxylic acid was added to a mixture of pyridine (118.5 g) and water (150 ml) at 30° to 33.5° C. under stirring. The resultant mixture was immediately poured into a cold mixture of isopropyl alcohol (900 ml) and diisopropyl ether (1.2 l) under cooling in an ice-bath and stirring. The resulting precipitate was filtered, washed with isopropyl alcohol and diisopropyl ether and then redissolved in water (1.0 l). An insoluble material was filtered off and the filtrate was passed through a column packed with acidic alumina (150 g). The eluate (1.38 l) was concentrated to about 60 g of weight under reduced pressure and stirred for 30 minutes under cooling in an ice-bath. The resulting precipitate was filtered, washed with methanol and diisopropyl ether and dried to give 7-amino-3-(1-pyridiniomethyl)-3-cephem-4-carboxylate thiocyanate (12.56 g), mp. 175° to 180° C. (dec.).

IR (Nujol): 2600–2300, 2050, 1790, 1650, 1630, 1560, 1150, 1045 cm$^{-1}$.

NMR (D$_2$O, δ): 3.33 and 3.67 (2H, ABq, J=18 Hz), 5.12 (1H, d, J=4 Hz), 5.30 (1H, d, J=4 Hz), 5.33 and 5.51 (2H, ABq, J=14 Hz), 7.84–8.24 (2H, m), 8.4–8.7 (1H, m), 8.75–9.03 (2H, m).

PREPARATION 19

To a mixture of 7-aminocephalosporanic acid (40 g) and potassium thiocyanate (15.7 g) in acetonitrile (200 ml) was added dropwise trifluoromethanesulfonic acid (40 ml) below 15° C. under cooling in an ice-bath and stirring, which was continued for 30 minutes at 5° to 15° C. and for 40 minutes at ambient temperature. The reaction mixture was poured into cold water (400 ml) and stirred for 30 minutes. The resulting precipitate was filtered, washed with water and acetone and dried to give 7-amino-3-cyanothiomethyl-3-cephem-4-carboxylic acid (26.2 g), mp. 175° to 180° C. (dec.).

IR (Nujol): 3170, 2600, 2350, 2160, 1800, 1615, 1530 cm$^{-1}$.

NMR (D$_2$O+DCl, δ): 3.80 (2H, s), 4.30 (2H, s) 5.20 (1H, d, J=5 Hz), 5.40 (1H, d, J=5 Hz).

EXAMPLE 5

To a suspension of 7-amino-3-(1-pyridiniomethyl)-3-cephem-4-carboxylate dihydrochloride dihydrate (56 g) in methylene chloride (1.12 l) was added trimethylsilylacetamide (280 g) and the mixture was stirred for 15 minutes at ambient temperature. The solution was cooled at −20° C. and 2-allyloxyimino-2-(5-dichlorophosphorylamino-1,2,4-thiadiazol-3-yl)acetyl chloride (syn isomer) (51 g) was added thereto at the same temperature under stirring, which was continued for 20 minutes at −13° to −10° C. and for 30 minutes at −5° to 0° C. The reaction mixture was poured into a saturated aqueous solution of sodium bicarbonate (1 l) under stirring and the aqueous layer was separated out. The organic layer was extracted twice with water (800 ml, 400 ml) and the extracts were combined with the aqueous layer. The combined aqueous solution was adjusted to pH 1.5 with 6N hydrochloric acid and the resulting precipitate was filtered off. The filtrate was subjected to column chromatography on nonionic adsorption resin "Diaion HP-20" (6 l). After the column was washed with water (10 l), the elution was carried out with 20% aqueous methanol. The fractions containing the object compound were combined, adjusted to pH 6.0 with 1N aqueous sodium hydroxide and concentrated to a weight of 318 g under reduced pressure. To the solution was added ion-exchange resin "Dowex 50 W 10 X(H$^+$form)" (prepared by the Dow Chemical Co.) (120 g) and the mixture was stirred for 5 minutes. The resin was filtered off, washed with water (142 ml), and the filtrate and the washings were combined. The combined solution was mixed with n-butanol (2.5 l) at −15° to −10° C. and to the resulting solution was added acetone (2.5 l) dropwise at −10° C. under stirring, which was continued for 40 minutes after removing the cooling bath. The resulting precipitate was filtered, washed with acetone (500 ml) and dried to give 7-[2-allyloxyimino-2-(5-phosphonoamino-1,2,4-thiadiazol-3-yl)acetamido]-3-(1-pyridiniomethyl)-3-cephem-4-carboxylate (syn isomer) (60.6 g), mp. 175° to 181° C. (dec.).

EXAMPLE 6

A suspension of crude 7-amino-3-(1-methyl-4-pyridiniothiomethyl)-3-cephem-4-carboxylate (purity: 59.9%, 14.68 g) in water (145 ml) was adjusted to pH 6.1 with triethylamine and acetone (73 ml) was added thereto. To the solution was added portionwise 2-ethoxyimino-2-(5-dichlorophosphorylamino-1,2,4-thiadiazol-3-yl)acetyl chloride (syn isomer) (10.20 g) at 3° to 7° C. under cooling in an ice-bath and stirring. The reaction mixture was kept at pH 6 to 7 with triethylamine during the addition. After stirring for one hour at 3° to 5° C., the reaction mixture was evaporated to remove acetone. The aqueous solution was adjusted to pH 6.0 with aqueous sodium bicarbonate, stirred for 30 minutes at ambient temperature and then adjusted to pH 1.5 with 6N hydrochloric acid. The resultant precipitate was filtered off and the filtrate was subjected to column chromatography on a nonionic adsorption resin "Diaion HP-20" (980 ml). After the column was washed with water (4 l), the elution was carried out with aqueous methanol (10%–30%). The eluates were combined, evaporated to remove methanol and lyophilized to give 7-[2-ethoxyimino-2-(5-phosphonoamino-1,2,4-thiadiazol-3-yl)acetamido]-3-(1-methyl-4-pyridiniothiomethyl)-3-cephem-4-carboxylate (syn isomer) (11.81 g), mp. 160° to 169° C. (dec.).

EXAMPLE 7

(a) To a mixture of sodium 2-methoxyimino-2-(2-dimethoxyphosphorylaminothiazol-4-yl)acetate (syn isomer) (3.20 g) and sodium bicarbonate (0.81 g) in N,N-dimethylacetamide (32 ml) was added methanesulfonyl chloride (1.88 g) under cooling in an ice-bath and stirring, which was continued for one hour and cooled to −23° C. To the cold reaction mixture was added a solution of 7-amino-3-(1-pyridiniomethyl-3-cephem-4-carboxylate dihydrochloride dihydrate (3.52 g) and trimethylsilylacetamide (17.6 g) in methylene chloride (35 ml) at −23° to −20° C. under stirring, which was continued for 30 minutes at −20° to −12° C. and for 25 minutes at −12° to 3° C. to give a mixture containing 7-[2-methoxyimino-2-(2-dimethoxyphosphorylaminothiazol-4-yl)acetamido]-3-(1-pyridiniomethyl)-3-cephem-4-carboxylate (syn isomer).

(b) To the mixture containing 7-[2-methoxyimino-2-(2-dimethoxyphosphorylaminothiazol-4-yl)acetamido]-3-(1-pyridiniomethyl)-3-cephem-4-carboxylate (syn isomer) was dropped trimethylsilyl bromide (14.80 g) at 3° to 8° C. under stirring, which was continued for 2.5 hours at ambient temperature. The reaction mixture was poured into diisopropyl ether (1.5 l) and the resultant resinous oil was separated by decantation. The oil was dissolved in water (300 ml), adjusted to pH 1 with 1N hydrochloric acid and subjected to column chromatography on a nonionic adsorption resin "Diaion HP-20" (320 ml). After the column was washed with water (1.4 l), the elution was carried out with 20% aqueous methanol. The fractions containing the object compound were collected, evaporated to remove methanol and lyophilized to give 7-[2-methoxyimino-2-(2-phosphonoaminothiazol-4-yl)acetamido]-3-(1-pyridiniomethyl)-3-cephem-4-carboxylate (syn isomer) (1.3 g), mp. 155° to 164° C. (dec.).

IR (Nujol): 3200, 1775, 1660, 1630, 1610, 1530, 1490, 1340, 1210, 1185, 1155, 1060, 1040 cm$^{-1}$.

NMR (D$_2$O+N$_a$HCO$_3$, δ): 3.25 and 3.70 (2H, ABq, J=18 Hz), 4.00 (3H, s), 5.31 (1H, d, J=5 Hz), 5.38 and 5.61 (2H, ABq, J=14 Hz), 5.88 (1H, d, J=5 Hz), 7.07 (1H, s), 8.19 (2H, m), 8.58 (1H, m), 8.98 (2H, m).

EXAMPLE 8

A suspension of 7-[2-allyloxyimino-2-(5-phosphonoamino-1,2,4-thiadiazol-3-yl)acetamido]-3-(1-pyridiniomethyl)-3-cephem-4-carboxylate (syn isomer) (5.81 g) in water (140 ml) was adjusted to pH 5.48 with 7.4N aqueous ammonia and the solution was lyophilized to give monoammonium salt of 7-[2-allyloxyimino-2-(5-phosphonoamino-1,2,4-thiadiazol-3-yl)acetamido]-3-(1-pyridiniomethyl)-3-cephem-4-carboxylate (syn isomer) (5.7 g), mp. 185° to 195° C. (dec.).

IR (Nujol): 3500–3100, 1770, 1673, 1605, 1535, 1287 cm$^{-1}$.

EXAMPLE 9

A suspension of 7-[2-allyloxyimino-2-(5-phosphonoamino-1,2,4-thiadiazol-3-yl)acetamido]-3-(1-pyridiniomethyl)-3-cephem-4-carboxylate (syn isomer) (5.81 g) in water (150 ml) was adjusted to pH 3.0 with 1N aqueous sodium hydroxide and the solution was lyophilized to give monosodium salt of 7-[2-allyloxyimino-2-(5-phosphonoamino-1,2,4-thiadiazol-3-yl)acetamido]-3-(1-pyridiniomethyl)-3-cephem-4-carboxylate (syn isomer) (6.0 g), mp. 200° to 210° C. (dec.).

IR (Nujol): 3500–3100, 1770, 1670, 1630, 1610, 1525 cm$^{-1}$.

EXAMPLE 10

A suspension of 7-[2-allyloxyimino-2-(5-phosphonoamino-1,2,4-thiadiazol-3-yl)acetamido]-3-(1-pyridiniomethyl)-3-cephem-4-carboxylate (syn isomer) (5.81 g) in water (150 ml) was adjusted to pH 6.0 with 1N aqueous sodium hydroxide and the solution was lyophilized to give disodium salt of 7-[2-allyloxyimino-2-(5-phosphonoamino-1,2,4-thiadiazol-3-yl)acetamido]-3-(1-pyridiniomethyl)-3-cephem-4-carboxylate (syn isomer) (6.1 g), mp. 205° to 215° C. (dec.).

IR (Nujol): 3500–3100, 1765, 1670, 1640–1600, 1530, 1290, cm$^{-1}$.

EXAMPLE 11

A suspension of 7-[2-allyloxyimino-2-(5-phosphonoamino-1,2,4-thiadiazol-3-yl)acetamido]-3-(1-pyridiniomethyl)-3-cephem-4-carboxylate (syn isomer) (5.81 g) in water (150 ml) was adjusted to pH 6.0 with calcium hydroxide (760 mg). After a small amount of insoluble material was filtered off, the filtrate was lyophilized to give calcium salt of 7-[2-allyloxyimino-2-(5-phosphonoamino-1,2,4-thiadiazol-3-yl)acetamido]-3-(1-pyridiniomethyl)-3-cephem-4-carboxylate (syn isomer) (6.2 g), mp.>230° C.

IR (Nujol): 3500–3100, 1770, 1670, 1635, 1610, 1525, 1290 cm$^{-1}$.

EXAMPLE 12

7-[2-allyloxyimino-2-(5 -phosphonoamino-1,2,4-thiadiazol-3-yl)acetamido]-3-(1-pyridiniomethyl)-3-cephem-4-carboxylate (syn isomer) (5.81 g) was reacted with potassium acetate to give dipotassium salt of 7-[2-allyloxyimino-2-(5-phosphonoamino-1,2,4-thiadiazol-3-yl)acetamido]-3-(1-pyridiniomethyl)-3-cephem-4-carboxylate (syn isomer) (6.40 g), mp. 143° to 148° C. (dec.).

IR (Nujol): 3150, 1760, 1660, 1605, 1520, 1280, 1150, 1010 cm$^{-1}$.

EXAMPLE 13

To a solution of monoammonium salt of 7-[2-allyloxyimino-2-(5-phosphonoamino-1,2,4-thiadiazol-3-yl)acetamido]-3-(1-pyridiniomethyl)-3-cephem-4-carboxylate (syn isomer) (500 mg) in water (2 ml) was added N,N-diethylacetamide (3.5 ml) and the mixture was allowed to stand for 3 days in a refrigerator. The resulting precipitate was collected by filtration, washed with 70% aqueous N,N-diethylacetamide and acetone successively and dried in air to give crystalline monoammonium salt of 7-[2-allyloxyimino-2-(5-phosphonoamino-1,2,4-thiadiazol-3-yl)acetamido]-3-(1-pyridiniomethyl)-3-cephem-4-carboxylate hexahydrates solvated with one molecule of N,N-diethylacetamide (syn isomer) (200 mg), mp. 90° to 95° C.

IR (Nujol): 3400, 3150, 1774, 1680, 1614, 1575, 1538, 1338, 1315, 1290, 1210 cm$^{-1}$.

NMR (D$_2$O, δ): 1.12 (3H, t, J=7 Hz), 1.18 (3H, t, J=7 Hz), 2.10 (3H, s), 3.20 and 3.70 (2H, ABq, J=18

Hz), 3.35 (2H, q, J=7 Hz), 3.42 (2H, q, J=7 Hz). 4.8 (2H, m), 5.30 (1H, d, J=5 Hz), 5.93 (1H, d, J=5 Hz), 5.1-6.5 (5H, m), 8.10 (2H, m), 8.60 (1H, m), 8.95 (2H, m).

Analysis for $C_{26}H_{36}N_9O_9PS_2 \cdot 6H_2O$:

|  | C | H | N | $H_2O$ |
|---|---|---|---|---|
| calc'd: | 38.00 | 5.89 | 15.34 | 13.15 |
| found: | 37.99 | 5.56 | 15.38 | 13.5 |

EXAMPLE 14

A solution of 7-[2-ethoxyimino-2-(5-phosphonoamino-1,2,4-thiadiazol-3-yl)acetamido]-3-(1-methyl-4-pyridiniothiomethyl)-3-cephem-4-carboxylate (syn isomer) (12.31 g) and sodium acetate (3.28 g) in water (60 ml) was added portionwise to acetone (1325 ml) at ambient temperature under stirring. The resultant precipitate was collected by filtration, washed with acetone and dried to give disodium salt of 7-[2-ethoxyimino-2-(5-phosphonoamino-1,2,4-thiadiazol-3-yl)acetamido]-3-(1-methyl-4-pyridiniothiomethyl)-3-cephem-4-carboxylate (syn isomer) (15.0 g), mp. 155° to 160° C. (dec.).

IR (Nujol): 3600–3100, 1760, 1675, 1605, 1530, 1285, 1225, 1115 cm$^{-1}$.

EXAMPLE 15

(a) A solution of 7-[2-propoxyimino-2-(5-phosphonoamino-1,2,4-thiadiazol-3-yl)acetamido]-3-(1-pyridiniomethyl)-3-cephem-4-carboxylate (syn isomer) (5.0 g) in water (50 ml) was adjusted to pH 4.2 with 1N ammonium hydroxide and lyophilized to give powdery monoammonium salt of 7-[2-propoxyimino-2-(5-phosphonoamino-1,2,4-thiadiazol-3-yl)acetamido]-3-(1-pyridiniomethyl)-3-cephem-4-carboxylate (syn isomer) (4.88 g).

(b) The monoammonium salt as obtained above (1.0 g) was dissolved in water (4 ml) and N,N-diethylacetamide (12 ml) was added thereto. The mixture was allowed to stand at ambient temperature to precipitate crystals and was further ice-cooled for one hour. The precipitating crystals were collected by filtration, in turn washed with a cold 80% aqueous solution of N,N-diethylacetamide (1.5 ml) and acetone and dried to give crystalline monoammonium salt of 7-[2-propoxyimino-2-(5-phosphonoamino-1,2,4-thiadiazol-3-yl)acetamido]-3-(1-pyridiniomethyl)-3-cephem-4-carboxylate solvated with one molecule of N,N-diethylacetamide (syn isomer) (950 mg), mp. 80° to 85° C.

IR (Nujol): 3400, 3200, 1770, 1680, 1620, 1540, 1490, 1340, 1210, 1150, 1070, 1050, 1020, 1000, 930 cm$^{-1}$.

NMR (D$_2$O, δ): 0.90 (3H, t, J=7 Hz), 1.08 (3H, t, J=7 Hz), 1.17 (3H, t, J=7 Hz), 1.53-1.98 (2H, m). 2.10 (3H, s), 3.30 (2H, t, J=7 Hz), 3.33 (2H, t, J=7 Hz), 3.17 and 3.70 (2H, ABq, J=18 Hz), 4.27 (2H, t, J=7 Hz), 5.30 (1H, d, J=5 Hz), 5.30 and 5.63 (2H, ABq, J=14 Hz), 5.90 (1H, d, J=5 Hz), 8.10 (2H, m), 8.58 (1H, m), 8.97 (2H, m).

EXAMPLE 16

The following compounds were obtained according to similar manners to those of aforesaid Examples.

(1) 7-[2-Propoxyimino-2-(5-phosphonoamino-1,2,4-thiadiazol-3-yl)acetamido]-3-(1-pyridiniomethyl)-3-cephem-4-carboxylate (syn isomer), mp. 177° to 182° C. (dec.).

IR (Nujol): 3200, 1780, 1650, 1630, 1520, 1485 cm$^{-1}$

NMR (D$_2$O, δ): 0.90 (3H, t, J=7 Hz), 1.47-2.0 (2H, m), 3.23 and 3.77 (2H, ABq, J=18 Hz), 4.27 (2H, t, J=7 Hz), 5.33 (1H, d, J=5 Hz), 5.37 and 5.77 (2H, ABq, J=14 Hz), 5.93 (1H, d, J=5 Hz), 8.10 (2H, m), 8.58 (1H, m), 8.95 (2H, m)

(2) 7-[2-Ethoxyimino-2-(5-phosphonoamino-1,2,4-thiadiazol-3-yl)acetamido]-3-(4-methoxy-1-pyridiniomethyl)-3-cephem-4-carboxylate (syn isomer), mp. 165° to 170° C. (dec.).

IR (Nujol): 3200, 1780, 1670, 1640, 1570, 1520 cm$^{-1}$.

NMR (D$_2$O, δ): 1.30 (3H, t, J=7 Hz), 3.30 and 3.63 (2H, ABq, J=18 Hz), 4.10 (3H, s), 4.33 (2H, q, J=7 Hz), 5.20 and 5.47 (2H, ABq, J=14 Hz), 5.28 (1H, d, J=5 Hz), 5.88 (1H, d, J=5 Hz), 7.43 (2H, d, J=7 Hz), 8.65 (2H, d, J=7 Hz).

(3) 7-[2-Ethoxyimino-2-(5-phosphonoamino-1,2,4-thiadiazol-3-yl)acetamido]-3-(3-chloro-1-pyridiniomethyl)-3-cephem-4-carboxylate (syn isomer), mp. 170° to 175° C. (dec.).

IR (Nujol): 3200, 2300, 1775, 1670, 1630, 1510 cm$^{-1}$.

NMR (D$_2$O, δ): 1.30 (3H, t, J=7 Hz), 3.35 and 3.73 (2H, ABq, J=14 Hz), 4.33 (2H, q, J=7 Hz), 5.32 (1H, d, J=5 Hz), 5.43 and 5.78 (2H, ABq, J=14 Hz). 5.93 (1H, d, J=5 Hz), 7.93-8.27 (1H, m), 8.53-8.80 (1H, m), 8.87-9.08 (1H, m), 9.17 (1H, broad s).

PREPARATION 20

Phosphorus pentachloride (21.98 g) was dissolved in methylene chloride (270 ml) at room temperature and cooled at −20° C. To the mixture were successively added methyl 2-ethoxyimino-2-(5-amino-1,2,4-thiadiazol-3-yl)acetate (syn isomer) (13.5 g) and pyridine (13.91 g) under stirring and keeping below −10° C. The mixture was stirred for 30 minutes and poured into 1N aqueous hydrochloric acid (176 ml). The organic layer was separated out, washed with a saturated aqueous solution of sodium chloride, dried and evaporated under reduced pressure. The resulting precipitates were collected by filtration, washed with diisopropyl ether and dried to give methyl 2-ethoxyimino-2-(5-dichlorophosphorylamino-1,2,4-thiadiazol-3-yl)acetate (syn isomer) (6.93 g). The crude product was used to the following reaction without further purification.

PREPARATION 21

To a cold solution of methyl 2-ethoxyimino-2-(5-dichlorophosphorylamino-1,2,4-thiadiazol-3-yl)acetate (syn isomer) (600 mg) in tetrahydrofuran was added aqueous conc.ammonia (0.48 ml) and the mixture was stirred for 30 minutes under cooling in an ice-bath. The reaction mixture was evaporated, diluted with an aqueous solution of sodium chloride (20 ml) and extracted with ethyl acetate. The extract was dried and evaporated. The residue was triturated in a mixed solvent of tetrahydrofuran and diisopropyl ether and the resulting precipitates were filtered, washed with diisopropyl ether to give methyl 2-ethoxyimino-2-(5-diaminophosphorylamino-1,2,4-thiadiazol-3-yl)acetate (syn isomer) (418 mg). The crude product was recrystallized from acetonitrile, mp 191° to 193° C. (dec.).

IR (Nujol): 3200, 3130, 1755, 1515, 1275, 1230 cm$^{-1}$.

NMR (DMSO-d$_6$+D$_2$O, δ): 1.21 (3H, t, J=7 Hz), 3.80 (3H, s), 4.22 (2H, q, J=7 Hz).

Anal. Calcd. for $C_7H_{13}N_6O_4PS$: C, 27.28; H, 4.25; N, 27.26. Found: C, 26.88; H, 4.12; N, 26.57.

PREPARATION 22

To a suspension of phosphorus pentachloride (48.59 g) in methylene chloride (630 ml) were added methyl 2-allyloxyimino-2-(5-amino-1,2,4-thiadiazol-3-yl)acetate (syn isomer) (31.44 g) at −25° C. and then pyridine (30.76 g) at −20° to −11° C. under stirring, which was continued for 30 minutes at −10° to −3° C. The reaction mixture was poured into a mixture of 1N aqueous hydrochloric acid (390 ml) and crushed ice. The organic layer was separated out, washed with a saturated aqueous solution of sodium chloride, dried and evaporated to dryness. The residue was triturated in diisopropyl ether to give methyl 2-allyloxyimino-2-(5-dichlorophosphorylamino-1,2,4-thiadiazol-3-yl)acetate (syn isomer) (29.02 g). The crude product was used to the following reaction without further purification.

PREPARATION 23

To a solution of methyl 2-allyloxyimino-2-(5-dichlorophosphorylamino-1,2,4-thiadiazol-3-yl)acetate (syn isomer) (359 mg) in methylene chloride (3.6 ml) were added pyridine (79 mg) at −9° C. and then a solution of ethanol (46 mg) in methylene chloride (2 ml). The mixture was stirred for 30 minutes at −11° to −10° C., for 25 minutes at −10° to 0° C. and for one hour and 40 minutes at room temperature. The reaction mixture was chilled in an ice-bath and morpholine (174 mg) was added thereto under stirring, which was continued for 50 minutes at room temperature. Water (5 ml) was added to the mixture. The organic layer was separated out, washed with a saturated aqueous solution of sodium chloride, dried and evaporated to dryness. The residue was subjected to column chromatography on silica gel (10 g). The elution was carried out with a mixed solvent (ethyl acetate/chloroform=2/1). The fractions containing the object compound were collected and evaporated to dryness to give methyl 2-allyloxyimino-2-[5-(ethoxy)(morpholino)phosphorylamino-1,2,4-thiadiazol-3-yl]acetate (syn isomer) (137 mg), oil.

IR (Nujol): 3100, 3000, 1750, 1530, 1390 cm$^{-1}$.

NMR (CDCl$_3$, δ): 1.37 (3H, t, J=7 Hz), 3.20 (4H, m), 3.67 (4H, m), 3.96 (3H, s), 4.18 (2H, m), 4.78 (2H, d, J=5 Hz), 5.43-5.10 (2H, m), 5.78-6.20 (1H, m).

PREPARATION 24

To a solution of methyl 2-allyloxyimino-2-(5-dichlorophosphorylamino-1,2,4-thiadiazol-3-yl)acetate (syn isomer) (5.0 g) in methylene chloride (100 ml) were successively added pyridine (3.3 g) and a solution of ethanol in methylene chloride (100 ml) under cooling at −35° C. to −25° C. and stirring. The mixture was stirred for 20 minutes at −20° to −10° C., for 30 minutes at 5° C. and then for two hours at room temperature, and poured into water (100 ml). The organic layer was separated, washed with 1N aqueous hydrochloric acid and a saturated aqueous solution of sodium chloride, dried over magnesium sulfate and evaporated to dryness under reduced pressure to give methyl 2-allyloxyimino-2-(5-diethoxyphosphorylamino-1,2,4-thiadiazol-3-yl)acetate (syn isomer) (5.25 g) as yellow oil.

IR (Film): 3500, 3100, 3000, 2900, 2800, 1750, 1600, 1530, 1510 cm$^{-1}$.

NMR (CDCl$_3$, δ): 1.37 (6H, t, J=7 Hz), 3.95 (3H, s), 4.22 (4H, m), 4.68-4.90 (2H, m), 5.07-5.55 (2H, m), 5.67-6.37 (1H, m), 6.85-7.40 (1H, m).

PREPARATION 25

The following compounds were obtained according to similar manners to those of Preparation 3 and 11.

(1) Sodium 2-ethoxyimino-2-(5-diaminophosphorylamino-1,2,4-thiadiazol-3-yl)acetate (syn isomer), mp 194° to 197° C. (dec.).

IR (Nujol): 3250, 1610, 1530, 1400, 1200 cm$^{-1}$.

NMR (DMSO-d$_6$+D$_2$O, δ): 1.20 (3H, t, J=7 Hz), 4.04 (2H, q, J=7 Hz).

(2) Sodium 2-allyloxyimino-2-[5-(ethoxy)(morpholino)phosphorylamino-1,2,4-thiadiazol-3-yl]acetate (syn isomer), mp 172° to 177° C. (dec.).

IR (Nujol): 3400, 1620, 1530, 1265, 1115 cm$^{-1}$.

NMR (DMSO-d$_6$, δ): 1.34 (3H, t, J=7 Hz), 3.17 (4H, m), 3.60 (4H, m), 4.12 (2H, m), 4.63 (2H, d, J=5 Hz), 4.92-5.63 (2H, m), 5.67-6.35 (1H, m).

(3) Sodium 2-allyloxyimino-2-(5-diethoxyphosphorylamino-1,2,4-thiadiazol-3-yl)acetate (syn isomer), mp 156° to 162° C. (dec.).

IR (Nujol): 1710, 1610, 1535, 1400 cm$^{-1}$.

NMR (DMSO-d$_6$+D$_2$O, δ): 1.22 (6H, t, J=7 Hz), 4.02 (4H, m), 4.55 (2H, d, J=5 Hz), 5.00-5.50 (2H, m), 5.67-6.25 (1H, m).

EXAMPLE 17

To a mixture of sodium 2-ethoxyimino-2-(5-diaminophosphorylamino-1,2,4-thiadiazol-3-yl)acetate (syn isomer) (2.10 g) and sodium bicarbonate (1.12 g) in N,N-dimethylacetamide (21 ml) was added methanesulfonyl chloride (1.03 ml) under cooling in an ice-bath and stirring, which was continued for one hour and 45 minutes and cooled to −20° C. To the cold reaction mixture was added a solution of 7-amino-3-(1-pyridiniomethyl)-3-cephem-4-carboxylate dihydrochloride dihydrate (2.39 g) and monotrimethylsilylacetamide (11.96 g) in methylene chloride (48 ml) at −18° C. under stirring, which was continued for 30 minutes at −18° to −12° C. and for 30 minutes at −10° to 0° C. The reaction mixture was poured into diisopropyl ether (700 ml) and the resulting precipitates were separated by decantation. The residue was dissolved in water (100 ml), adjusted to pH 3.8 with 1N hydrochloric acid and subjected to column chromatography on a non-ionic adsorption resin "Diaion HP-20" (105 ml). After the column was washed with water (500 ml), the elution was carried out with 20% aqueous methanol. The fractions containing the object compound were collected, evaporated to remove methanol and lyophilized to give 7-[2-ethoxyimino-2-(5-diaminophosphorylamino-1,2,4-thiadiazol-3-yl)acetamido]-3-(1-pyridiniomethyl)-3-cephem-4-carboxylate (syn isomer) (1.11 g), mp 123° to 132° C. (dec.).

IR (Nujol): 3200, 1770, 1660, 1610, 1510 cm$^{-1}$.

NMR (DMSO-d$_6$+D$_2$O, δ): 1.25 (3H, t, J=7 Hz), 3.12, 3.55 (2H, ABq, J=17 Hz), 4.19 (2H, q, J=7 Hz), 5.10 (1H, d, J=5 Hz), 5.23, 5.67 (2H, ABq, J=14 Hz), 5.75 (1H, d, J=5 Hz), 8.17 (2H, m), 8.63 (1H, m), 9.41 (2H, d, J=7 Hz).

EXAMPLE 18

The following compounds were obtained according to similar manners to those of aforesaid Examples.

(1) 7-[2-Allyloxyimino-2-{5-(ethoxy)(morpholino)phosphorylamino-1,2,4-thiadiazol-3-yl}acetamido]-3-(1-pyridiniomethyl)-3-cephem-4-carboxylate (syn isomer), mp 132° to 141° C. (dec.).

IR (Nujol): 3400, 3200, 1700, 1670, 1610, 1510 cm$^{-1}$.

NMR (DMSO-d$_6$+D$_2$O, δ): 1.22 (3H, t, J=8 Hz), 3.00 (4H, m), 3.46 (4H, m), 3.99 (2H, m), 4.59 (2H, d, J=5 Hz), 4.90–6.20 (4H, m), 5.00 (1H, d, J=5 Hz), 5.66 (1H, d, J=5 Hz), 8.06 (2H, m), 8.50 (1H, m), 9.26 (2H, d, J=5 Hz).

(2) 7-[2-Ethoxyimino-2-{5-(amino)(hydroxy)phosphorylamino-1,2,4-thiadiazol-3-yl}acetamido]-3-(1-pyridiniomethyl)-3-cephem-4-carboxylate (syn isomer), mp 150° to 157° C. (dec.).

IR (Nujol): 3200, 1775, 1660, 1630, 1520 cm$^{-1}$.

(3) 7-[2-Allyloxyimino-2-(5-O-ethylphosphonoamino-1,2,4-thiadiazol-3-yl)acetamido]-3-(1-pyridiniomethyl)-3-cephem-4-carboxylate (syn isomer), mp 157° to 164° C. (dec.).

IR (Nujol): 3200, 1780, 1670, 1630, 1510 cm$^{-1}$.

(4) 7-[2-Allyloxyimino-2-(5-diethoxyphosphorylamino-1,2,4-thiadiazol-3-yl)acetamido]-3-(1-pyridiniomethyl)-3-cephem-4-carboxylate (syn isomer), mp 124° to 131° C. (dec.).

IR (Nujol): 3400, 3200, 1775, 1670, 1610, 1520 cm$^{-1}$.

NMR (D$_2$O, δ): 1.38 (6H, t, J=7 Hz), 3.27, 3.70 (2H, ABq, J=18 Hz), 4.29 (4H, m), 4.87 (2H, m), 5.10–5.70 (4H, m), 5.77–6.16 (1H, m), 5.33 (1H, d, J=5 Hz), 5.95 (1H, d, J=5 Hz), 8.16 (2H, m), 8.59 (1H, m), 9.05 (2H, m).

EXAMPLE 19

To a cold aqueous 1N hydrochloric acid was added 7-[2-ethoxyimino-2-(5-diaminophosphorylamino-1,2,4-thiadiazol-3-yl)acetamido]-3-(1-pyridiniomethyl)-3-cephem-4-carboxylate (syn isomer) (1.0 g) and the mixture was stirred for seven minutes in an ice-bath. The reaction mixture was adjusted to pH 2 with aqueous sodium bicarbonate and subjected to column chromatography on a non-ionic adsorption resin "Diaion HP-20" (100 ml). After the column was washed with water (400 ml), the elution was carried out with 10% aqueous methanol. The fractions containing the object compound were collected, concentrated to about 10 ml under reduced pressure and poured into acetone (100 ml). The resulting precipitates were collected by filtration, washed with acetone and dried to give 7-[2-ethoxyimino-2-{5-(amino)(hydroxy)phoshorylamino-1,2,4-thiadiazol-3-yl}acetamido]-3-(1-pyridiniomethyl)-3-cephem-4-carboxylate (syn isomer) (0.37 g), mp 150° to 157° C. (dec.).

IR (Nujol): 3200, 1775, 1660, 1630, 1520 cm$^{-1}$.

NMR (DMSO-d$_6$+D$_2$O, δ): 1.19 (3H, t, J=7 Hz), 3.00–3.80 (2H, m), 4.12 (2H, q, J=7 Hz), 5.10–5.80 (2H, m), 5.77 (1H, d, J=5 Hz), 8.18 (2H, m), 8.55 (2H, m), 9.23 (2H, m).

EXAMPLE 20

A solution of 7-[2-allyloxyimino-2-{5-(ethoxy)(morpholino)phosphorylamino-1,2,4-thiadiazol-3-yl}acetamido]-3-(1-pyridiniomethyl)-3-cephem-4-carboxylate (syn isomer) (2.80 g) in 1N aqueous hydrochloric acid (28 ml) was stirred for 4 hours at 40° C. The reaction mixture was diluted with water (70 ml) and subjected to column chromatography on non-ionic adsorption resin "Diaion HP-20" (112 ml). After the column was washed with water (500 ml), the elution was carried out with 30% aqueous methanol. The fractions containing the object compound were combined, concentrated to about 20 ml under reduced pressure. The residue was poured to acetone (300 ml) and the resulting precipitates were filtered, washed with acetone and dried to give 7-[2-allyloxyimino-2-(5-O-ethylphosphonoamino-1,2,4-thiadiazol-3-yl)acetamido]-3-(1-pyridiniomethyl)-3-cephem-4-carboxylate (syn isomer) (1.16 g), mp 157° to 164° C. (dec.).

IR (Nujol): 3200, 1780, 1670, 1630, 1510 cm$^{-1}$.

NMR (D$_2$O, δ): 1.22 (3H, t, J=7 Hz), 3.30, 3.72 (2H, ABq, J=19 Hz), 3.96 (2H, m), 5.10–6.20 (5H, m), 5.22 (1H, d, J=5 Hz), 5.93 (1H, d, J=5 Hz), 8.10 (2H, m), 8.61 (1H, m), 8.97 (2H, d, J=6 Hz).

What we claim is:

1. A cephem compound of the formula:

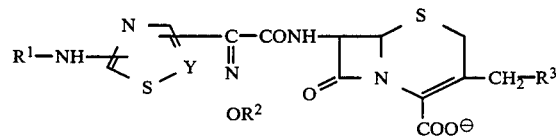

wherein R$^1$ is phosphono, dihalophosphoryl, di(lower)alkoxyphosphoryl, O-lower alkylphosphono, diaminophosphoryl, (amino)(hydroxy)phosphoryl or (lower alkoxy)(morpholino)phoshoryl, R$^2$ is lower alkyl or lower alkenyl, R$^3$ is a group of the formula:

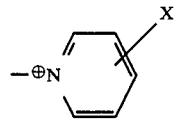

wherein X is hydrogen, halogen or lower alkoxy, or a group of the formula:

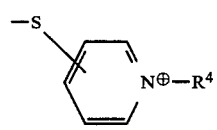

wherein R$^4$ is lower alkyl, and
Y is N or CH;
and pharmaceutically acceptable salts thereof.

2. Syn isomer of a compound of claim 1, wherein

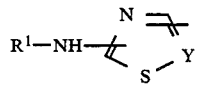

group is

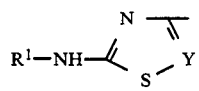

3. A compound of claim 2, wherein R$^3$ is a group of the formula:

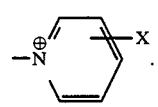

4. A compound of claim 3, wherein R$^1$ is phosphono, dimethoxyphosphoryl, diethoxyphosphoryl, O-ethylphosphono, diaminophosphoryl, (amino)(hydroxy)- phosphoryl or (ethoxy)(morpholino)phosphoryl, $R^2$ is methyl, ethyl, propyl or allyl and X is hydrogen, 3-chloro or 4-methoxy.

5. A compound of claim 4, which is selected from the compound consisting of:

7-[2-ethoxyimino-2-(5-phosphonoamino-1,2,4-thiadiazol-3-yl)acetamido]-3-(1-pyridiniomethyl)-3-cephem-4-carboxylate (syn isomer), 7-[2-ethoxyimino-2-(5-phosphonoamino-1,2,4-thiadiazol-3-yl)acetamido]-3-(4-methoxy-1-pyridiniomethyl)-3-cephem-4-carboxylate (syn isomer), 7-[2-ethoxyimino-2-(5-phosphonoamino-1,2,4-thiadiazol-3-yl)acetamido]-3-(3-chloro-1-pyridiniomethyl)-3-cephem-4-carboxylate (syn isomer), 7-[2-allyloxyimino-2-(5-phosphonoamino-1,2,4-thiadiazol-3-yl)acetamido]-3-(1-pyridiniomethyl)-3-cephem-4-carboxylate (syn isomer), monoammonium salt of 7-[2-allyloxyimino-2-(5-phosphonoamino-1,2,4-thiadiazol-3-yl)acetamido]-3-(1-pyridiniomethyl)-3-cephem-4-carboxylate (syn isomer), 7-[2-methoxyimino-2-(2-phosphonoaminothiazol-4-yl)acetamido]-3-(1-pyridiniomethyl)-3-cephem-4-carboxylate (syn isomer), 7-[2-propoxyimino-2-(5-phosphonoamino-1,2,4-thiadiazol-3-yl)acetamido]-3-(1-pyridiniomethyl)-3-cephem-4-carboxylate (syn isomer), 7-[2-ethoxyimino-2-(5-diaminophosphorylamino-1,2,4-thiadiazol-3-yl)acetamido]-3-(1-pyridinomethyl)-3-cephem-4-carboxylate (syn isomer), 7-[2-ethoxyimino-2-{5-(amino)(hydroxy)phoshorylamino-1,2,4-thiadiazol-3-yl}acetamido]-3-(1-pyridiniomethyl)-3-cephem-4-carboxylate (syn isomer), 7-[2-allyloxyimino-2-(5-diethoxyphosphorylamino-1,2,4-thiadiazol-3-yl)acetamido]-3-(1-pyridiniomethyl)-3-cephem-4-carboxylate (syn isomer), 7-[2-allyloxyimino-2-(O-ethylphosphonoamino-1,2,4-thiadiazol-3-yl)acetamido]-3-(1-pyridiniomethyl)-3-cephem-4-carboxylate (syn isomer) and 7-[2-allyloxyimino-2-{5-(ethoxy)(morpholino)phosphorylamino-1,2,4-thiadiazol-3-yl}acetamido]-3-(1-pyridiniomethyl)-3-cephem-4-carboxylate (syn isomer).

6. A compound of claim 2, wherein $R^1$ is phosphono, $R^2$ is lower alkyl, $R^3$ is a group of the formula:

and Y is N.

7. A compound of claim 6, which is 7-[2-ethoxyimino-2-(5-phosphonoamino-1,2,4-thiadiazol-3-yl)acetamido]-3-(1-methyl-4-pyridiniothiomethyl)-3-cephem-4-carboxylate (syn isomer).

8. A pharmaceutical antibacterial composition comprising an effective amount of a compound of claim 1 in association with a pharmaceutically acceptable, substantially non-toxic carrier or excipient.

* * * * *